United States Patent
Volpe

(10) Patent No.: US 12,048,762 B2
(45) Date of Patent: Jul. 30, 2024

(54) NICOTINE PARTICLES

(71) Applicant: PHILIP MORRIS PRODUCTS S.A., Neuchâtel (CH)

(72) Inventor: Nicolo Volpe, Lausanne (CH)

(73) Assignee: Philip Morris Products S.A., Neuchâtel (CH)

(*) Notice: Subject to any disclaimer, the term of this patent is extended or adjusted under 35 U.S.C. 154(b) by 0 days.

(21) Appl. No.: 17/939,348

(22) Filed: Sep. 7, 2022

(65) Prior Publication Data

US 2023/0000767 A1    Jan. 5, 2023

Related U.S. Application Data

(62) Division of application No. 16/309,787, filed as application No. PCT/IB2017/053710 on Jun. 21, 2017, now Pat. No. 11,458,093.

(30) Foreign Application Priority Data

Jun. 30, 2016 (EP) .................................. 16177156

(51) Int. Cl.
A61K 9/00 (2006.01)
A61K 9/16 (2006.01)
A61K 31/465 (2006.01)

(52) U.S. Cl.
CPC .......... *A61K 9/0075* (2013.01); *A61K 9/1617* (2013.01); *A61K 9/1623* (2013.01); *A61K 9/1682* (2013.01); *A61K 31/465* (2013.01)

(58) Field of Classification Search
CPC ... A61K 31/465; A61K 9/0075; A61K 9/1682
See application file for complete search history.

(56) References Cited

U.S. PATENT DOCUMENTS

| | | | |
|---|---|---|---|
| 4,655,231 A | 4/1987 | Ray | |
| 5,619,985 A | 4/1997 | Ohki | |
| 6,475,523 B1 | 11/2002 | Staniforth | |
| 6,799,576 B2 | 10/2004 | Farr | |
| 8,381,739 B2 | 2/2013 | Gonda | |
| 9,463,161 B2 | 10/2016 | Vehring et al. | |
| 2004/0118007 A1 | 6/2004 | Chickering, III et al. | |
| 2007/0104658 A1 | 5/2007 | Batycky et al. | |
| 2007/0292519 A1 | 12/2007 | Piskorz | |
| 2008/0127972 A1 | 6/2008 | Morton | |
| 2008/0138398 A1 | 6/2008 | Gonda | |
| 2008/0226736 A1* | 9/2008 | Caponetti | A61K 9/0078 514/649 |
| 2008/0286340 A1 | 11/2008 | Andersson et al. | |
| 2012/0020887 A1 | 1/2012 | Batycky | |
| 2012/0042886 A1 | 2/2012 | Piskorz | |
| 2012/0135969 A1 | 5/2012 | Weiler | |
| 2013/0251779 A1 | 9/2013 | Svandal et al. | |
| 2014/0261474 A1 | 9/2014 | Gonda | |
| 2014/0345631 A1 | 11/2014 | Bowen et al. | |
| 2015/0283070 A1* | 10/2015 | Stenzler | A61K 31/045 514/343 |

FOREIGN PATENT DOCUMENTS

| | | |
|---|---|---|
| CN | 101106975 | 1/2008 |
| JP | A2012509922 | 4/2012 |
| JP | A2015509788 | 4/2015 |
| JP | A2016515640 | 5/2016 |
| RU | 2497507 | 11/2013 |
| WO | 1999045902 | 9/1999 |
| WO | 2001013893 | 3/2001 |
| WO | 2007045689 | 4/2007 |
| WO | 2010060875 | 6/2010 |
| WO | 2013130767 | 9/2013 |
| WO | 2014167023 | 10/2014 |
| WO | 2015173648 | 11/2015 |
| WO | WO 2015/166350 A2 | 11/2015 |
| WO | 2007125159 | 7/2017 |

OTHER PUBLICATIONS

Chinese Office Action for CN 201780035401.2 issued by the China National Intellectual Property Administration, Dec. 7, 2021; 22 pgs. including English translation.
Chinese Second Office Action for CN 201780035401.2 issued by the China National Intellectual Property Administration, May 7, 2022; 24 pgs. including English translation.
Japanese Decision of Final Rejection for JP Application No. 2018-563818, dated Jan. 17, 2022; 10 pgs. including English translation.
Ukraine Office Action for Application No. a 2018 10804 issued by the Ukraine Patent Office on Jan. 12, 2022; 10 pgs. including English translation.
International Search Report and Written Opinion for PCT/IB2017/053710, issued on Sep. 1, 2017, by the European Patent Office; 14 pgs.
European Search Report for EP 16177156.3, issued on Aug. 22, 2016; by the European Patent Office; 8 pgs.
Vehring, Reinhard "Pharmaceutical Particle Engineering via Spray Drying," Pharmaceutical Research, May 2008; 25(5):999-1022.
Russian Office Action issued by the Russian Patent Office for RU 2018144108, issued by the Russian patent Office on Jul. 10, 2020; 16 pgs. including English Translation.
Korean Office Action issued by the Korean Intellectual Property Office on Dec. 21, 2022, 12 pgs. including English translation.
Brazilian Office Action for BR 112018075017-4 issued by the Brazilian Patent Office on Jan. 29, 2024; 7 pgs. including English translation.

* cited by examiner

*Primary Examiner* — Michael B. Pallay
(74) *Attorney, Agent, or Firm* — Mueting Raasch Group

(57) ABSTRACT

A method includes combining nicotine with a liquid carrier to form a liquid mixture and spray drying the liquid mixture to form a first plurality of particles. The first pluralities of particles are then milled to form a second plurality of particles.

20 Claims, 1 Drawing Sheet

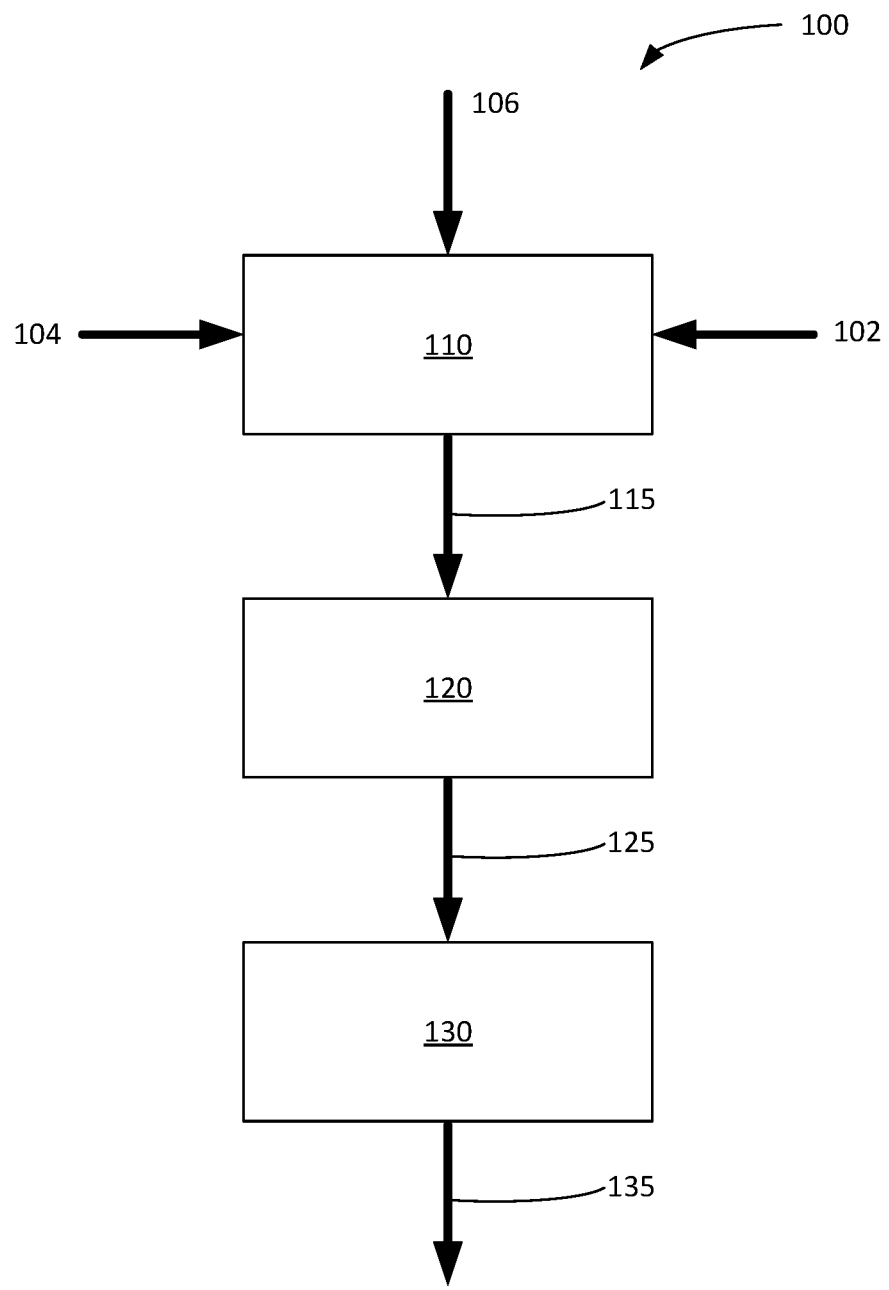

NICOTINE PARTICLES

This application is a divisional of U.S. Ser. No. 16/309,787, filed 12 Dec. 2018, which is the § 371 U.S. National Stage of International Application No. PCT/IB2017/053710, filed 21 Jun. 2017, which claims the benefit of European Application No. 16177156.3, filed 30 Jun. 2016, the disclosures of which are incorporated by reference herein in their entireties.

This disclosure relates to nicotine particles that are suitable for inhalation. The nicotine particles are formed by spray drying followed by milling.

Dry powder inhalers (DPI) are known and are used to treat respiratory diseases by delivering a dry powder comprising a pharmaceutically active compound, in aerosol form through inhalation to the patients' airways. In pharmaceutical dry powders, the active pharmaceutical ingredient (API) is usually agglomerated on the surface of larger carrier particles, such as lactose for example. DPI's operate complex mechanisms to ensure such agglomerates disperse, break up or disaggregate before the API is inhaled into the lungs.

It may be difficult to deliver nicotine particles to the lungs at inhalation at air flow rates that are within conventional smoking regime inhalation or air flow rates. Nicotine particles may have a tendency to agglomerate and stick to inhaler or processing surfaces, especially as a size of the nicotine particle deceases. Nicotine particles with an MMAD of less than about 10 micrometres tend to be increasingly thermodynamically unstable due to a high surface area to volume ratio, which provides an increasing surface free energy with this decreasing particle size, and consequently increases the tendency of particles to agglomerate and the strength of the agglomerate. Forming nicotine particles may be difficult and costly.

Nicotine particles may be irritating when inhaled and may induce a cough reflex. Cough suppressants such as menthol have been added to nicotine particle compositions. These cough suppressants may have a tendency to agglomerate the nicotine particles and cause stickiness of the composition. This may lead to handling and storage concerns of the nicotine particle compositions.

It would be desirable to provide nicotine particles that may reduce or mitigate a cough reflex when inhaled and provide an enhanced inhalation experience. It would be desirable that the nicotine particles be formed and processed easily and exhibit a stable particle size distribution. It may be desirable that the nicotine particles be free of a cough suppressant material.

Nicotine particles may be formed by spray drying a liquid mixture to form a first plurality of particles. The liquid mixture comprises nicotine. The liquid mixture may also comprise a sugar, or an amino acid, or both a sugar and amino acid. The liquid mixture may comprise a short peptide comprising 2 or 3 amino acid. The first plurality of particles is then milled to form a second plurality of particles.

The second plurality of nicotine particles may have a particle size distribution where about 90% the plurality of particles have a particle size of less than about 2.8 micrometres, and about 50% of the plurality of particles have a particle size of less than about 1.35 micrometres, and about 10% of the second plurality of particles having a particle size of less than about 0.65 micrometres.

Preferably the milling step is performed with a fluid energy mill. The fluid energy mill may decrease an average particle size or mass median aerodynamic diameter of the nicotine particles.

Advantageously, the method described herein utilizes a spray dryer to provide homogenous nicotine particles that can be further reduced in size with a fluid energy mill to achieve a specific and controlled particle size distribution. This method advantageously maximizes product yield in a cost effective manner. The final size distribution of the second plurality of nicotine particles may be stable over time and form a flowable composition. The final size distribution of the second plurality of nicotine particles is sufficient to deliver nicotine to the lungs at inhalation or air flow rates that are within conventional smoking regime inhalation or air flow rates, to provide an enhanced inhalation experience.

The term "nicotine" refers to nicotine and nicotine derivatives in any form, including but not limited to, a free-base nicotine, nicotine salt, or in a matrix such as a sugar matrix or organometallic complex.

The term "amino acid" refers to a single unmodified or modified amino acid moiety, preferably unmodified.

The term "short peptide" refers to a peptide comprising two or three amino acids.

The phrase "fluid energy milling" refers to particle size reduction by colliding particle streams. Fluid energy milling includes air jet milling or jet milling.

The phrase "plurality of particles" unless otherwise specified, means the first plurality of particles, the second plurality of particles, or both the first and the second plurality of particles.

The size of a particle, stated herein, preferably refers to the aerodynamic diameter of the particle. The aerodynamic diameter of a powder system is preferably measured with a cascade impactor. The term "MMAD" refers to the mass median aerodynamic diameter.

This disclosure relates to nicotine particles that are suitable for inhalation and methods for forming the same. These nicotine particles may provide for gentle or smooth inhalation without inducing or minimizing a cough reflex. The nicotine particles may be formed by spray drying a liquid mixture to form a first plurality of particles. The liquid mixture comprises nicotine. The liquid mixture may also comprise a sugar, or an amino acid, or both a sugar and amino acid. Spray drying the liquid mixture may form a homogenous first plurality of particles. The first plurality of particles may then be milled (preferably with a fluid energy mill) to form a second plurality of particles having a size distribution that is reduced as compared to the size distribution of the first plurality of particles. The second plurality of nicotine particles may have a particle size distribution where about 90% (by volume) of the plurality of particles have a particle size of less than about 2.8 micrometres, and about 50% of the plurality of particles have a particle size of less than about 1.35 micrometres, and about 10% of the second plurality of particles having a particle size of less than about 0.65 micrometres. The percentages relating to particle size distribution described herein are based on particle volume (% by volume). A dry powder composition may be formed form these nicotine particles. An inhalation delivery consumable element may contain the nicotine particles or dry powder composition described herein.

The combination of spray drying followed by milling (preferably fluid energy milling) advantageously provides nicotine particles that may be flowable, have a specific, controlled and stable particle size distribution and provide an enhanced inhalation experience. Spray drying forms a first plurality of particles having a first size distribution. Advantageously, milling or fluid energy milling decreases an average particle size of the particles. Milling or fluid energy milling utilizes the first plurality of particles and forms a second plurality of particles having a second size distribution. The second size distribution is preferably reduced as compared to the first size distribution.

The nicotine may be dissolved in the liquid carrier to form the liquid mixture. Sugar may be dissolved in the liquid carrier to form the liquid mixture. An amino acid may be dissolved in the liquid carrier to form the liquid mixture. A short peptide may be dissolved in the liquid carrier to form the liquid mixture.

Spray drying utilizes a spray or atomization nozzle to atomize a liquid mixture (under pressure) and evaporate liquid carrier from the liquid mixture. The resulting dry particles may be spheroid shaped within a designed particle size distribution.

Fluid energy milling is a size reduction unit operation that utilizes colliding fluid streams (for example gas or compressed gas or air) carrying particles. The colliding fluid streams provide particle to particle impact to facilitate size reduction. There are generally no moving parts in a fluid energy mill and generally no mechanical forces act on the particles during size reduction.

Fluid energy or jet mills are typically capable of reducing solids to particle sizes in the low-micron to submicron range. The size reduction energy is typically created by gas streams from horizontal grinding air nozzles. Typically, particles in the fluidized bed created by the gas streams are accelerated towards the center of the mill, colliding with slower moving particles or particles moving in a different direction. The gas streams and the particles carried in them typically create a violent turbulence and as the particles collide with one another they are reduced in size.

The second plurality of particles may be formed by fluid energy milling or colliding air streams with entrained nicotine particles. Preferably, the particle compositions of colliding air streams are substantially similar and homogenous. Fluid energy milling may increase the amount of respirable nicotine particles (particles able to reach the lungs) as compared to spray dried only nicotine particles. Fluid energy milling may increase this amount by at least about 10% or at least about 20% or at least 30%.

The fluid energy milling step may reduce the particle size or average particle size or particle size distribution by about 10% or greater, or about 20% or greater. Larger particles may be reduced a greater amount than smaller particles in the same size distribution. For example the 90% size threshold may be reduced (from the first size distribution 90% threshold to the second size distribution 90% threshold) by about 10% or greater, or about 20% or greater, or about 30% or greater, or in a range from about 10% to about 40%, or from about 20% to about 40%.

The fluid energy milling step may reduce the mass median aerodynamic diameter of the first plurality of particles to a mass median aerodynamic diameter of the second plurality of particles by a ratio of about 1.1:1 to about 10:1, or about 1.2:1 to about 5:1, or about 1.2:1 to about 3.6:1, or about 1.5:1 to about 3:1, or about 3:1, or about 2:1.

Preferably, the ratio of the mass median aerodynamic diameter of the first plurality of particles to the mass median aerodynamic diameter of the second plurality of particles is between about 1.1:1 to about 10:1, or about 1.2:1 to about 5:1, or about 1.2:1 to about 3.6:1, or about 1.5:1 to about 3:1, or about 3:1, or about 2:1.

The first plurality of particles may comprise about 90%, or about 95%, or about 98% of particles having an aerodynamic diameter of about 4.5 micrometres or less. The first plurality of particles may comprise at least about 50% of particles having an aerodynamic diameter of about 2.5 micrometres or less. The first plurality of particles may comprise at least about 10% of particles having an aerodynamic diameter of about 0.85 micrometres or less. The first plurality of particles may have a mass median aerodynamic diameter in a range from about 1 to about 4 micrometres. Substantially all of the first plurality of particles may have an aerodynamic diameter in a range from about 500 nanometers to about 5 micrometres.

Fluid energy milling reduces the size of the first plurality of particles to form a second plurality of particles. The second plurality of particles may comprise at least about 90%, or about 95%, or about 98% of particles having an aerodynamic diameter of about 3 micrometres or less, or 2.8 micrometres or less. The second plurality of particles may comprise at least about 50% of particles having an aerodynamic diameter of about 1.5 micrometres or less, or 1.35 micrometres or less. The second plurality of particles may comprise at least about 10% of particles having an aerodynamic diameter of about 0.7 micrometres or less, or 0.65 micrometres or less. The second plurality of particles may have a mass median aerodynamic diameter in a range from about 1 to about 2.5 micrometres. Substantially all of the second plurality of particles may have an aerodynamic diameter in a range from about 500 nanometers to about 3 micrometres.

The nicotine component of the particle may be a free base nicotine, a nicotine salt, or a combination thereof. The nicotine component may be a nicotine salt formed by combining nicotine or nicotine free base with an acid. The acid may be a stoichiometric amount of acid to the nicotine free base, or a stoichiometric excess of acid may be combined with the nicotine free base, or a stoichiometric excess of nicotine free base may be combined with the acid. A free base nicotine may be utilized without the addition of an acid.

The acid may be an organic acid, an inorganic acid, or a Lewis acid. Non-limiting examples of inorganic acids are hydrochloric, hydrobromic, hydroiodic, nitric, sulfuric, phosphoric, acetic, hexafluorophosphoric, and the like. Non-limiting examples of organic acids are levulinic, citric, gluconic, benzoic, propionic, butyric, sulfosalicylic, maleic, lauric, malic, fumaric, succinic, tartaric, amsonic, pamoic, mesylic, aspartic, formic, acetic, propionic, succinic, camphorsulfonic, fumaric, isethionic, lactic, mucic, para-toluenesulfonic, glycolic, glucuronic, maleic, furoic, glutamic, benzoic, anthranilic, salicylic, phenylacetic, pyruvic, mandelic, embonic (pamoic), methanesulfonic, ethanesulfonic, pantothenic, benzenesulfonic (besylate), stearic, sulfanilic, alginic, galacturonic, and the like. Non-limiting examples of Lewis acids are zinc chloride or zinc bromide ($ZnCl_2$/$ZnBr_2$). These can react with nicotine to form organometallic complexes.

Useful nicotine salts include, but are not limited to, nicotine pyruvate, nicotine citrate, nicotine aspartate, nicotine lactate, nicotine bitartrate, nicotine salicylate, nicotine fumarate, nicotine mono-pyruvate, nicotine glutamate or nicotine hydrochloride, for example. Preferred nicotine salts include, nicotine lactate, nicotine pyruvate, nicotine citrate, nicotine aspartate, or a combination thereof.

The pH of the plurality of particles (dissolved in water) may be in a range from about 5 to about 9. Preferably the pH is about 7.0 or higher or in a range from 7.0 to 9.0. A pH of 9 can be reached for a particle without organic acid, while a pH of 5.0 can be obtained with the use of a strong acid or diacid when forming the nicotine salt.

The plurality of particles may include an amino acid or peptide (preferably formed of three or less amino acids). The amino acid or peptide may reduce adhesion forces of the particles and mitigate or prevent agglomeration of the particles during formation or subsequent handling. The particles may form be a free flowing material and may possess a stable relative particle size distribution during processing, transport and storage.

Useful amino acids may include leucine, alanine, valine, isoleucine, methionine, phenylalanine, tyrosine, tryptophan, or a combination thereof. One preferred amino acid is leucine or a leucine isomer such as, L-leucine. A useful peptide includes trileucine, for example.

The plurality of particles may include a sugar. Sugar refers to simple sugars, monosaccharides, disaccharides, and polysaccharides. Without limitation, examples of suitable sugars are lactose, sucrose, raffinose, trehalose, fructose, dextrose, glucose, maltose, mannitol, or combinations thereof. Preferred sugars include trehalose or mannitol.

The plurality of particles may contain less than about 30 wt % nicotine. The plurality of particles may contain about 25 wt % or less nicotine or from about 15 to about 25 wt % nicotine. The plurality of particles may contain from about 1 to about 20 wt % nicotine or from about 10 to about 20 wt % nicotine, or from about 5 to 15 wt % nicotine. The plurality of particles may contain from about 1 to about 10 wt % nicotine or from about 5 to about 10 wt % nicotine.

The plurality of particles may contain about 1 to about 10 wt % amino acid. The plurality of particles may contain about 3 to about 7 wt % amino acid. The plurality of particles may contain from about 5 wt % amino acid. The addition of the amino acid, especially L-leucine for example, to the particles may reduce agglomeration or adherence to processing surfaces.

The plurality of particles may contain about 60 to about 95 wt % sugar. The plurality of particles may contain about 70 to about 90 wt % sugar.

Useful nicotine particles include an amino acid being leucine, a sugar being trehalose, and a nicotine salt being nicotine lactate. The nicotine content may be from about 5 to about 15 wt % or about 9.5 wt %. The leucine content may be from about 3 to about 7 wt % or about 5 wt %. The molar ratio of acid:nicotine may be about 1:1.

Useful nicotine particles include an amino acid being leucine, a sugar being trehalose, and a nicotine salt being nicotine citrate. The nicotine content may be from about 5 to about 15 wt % or about 9.6 wt %. The leucine content may be from about 3 to about 7 wt % or about 5 wt %. The molar ratio of acid:nicotine may be about 0.25:1.

Useful nicotine particles include an amino acid being leucine, a sugar being trehalose, and a nicotine salt being nicotine pyruvate. The nicotine content may be from about 5 to about 15 wt % or about 9.8 wt %. The leucine content may be from about 3 to about 7 wt % or about 5 wt %. The molar ratio of acid:nicotine may be about 0.6:1.

Useful nicotine particles include an amino acid being leucine, a sugar being trehalose, and a nicotine salt being nicotine aspartate. The nicotine content may be from about 5 to about 15 wt % or about 9.3 wt %. The leucine content may be from about 3 to about 7 wt % or about 5 wt %. The molar ratio of acid:nicotine may be about 0.6:1.

The particles may be formed by: (1) combining a nicotine, and optionally a sugar and an amino acid or peptide in a liquid carrier to form a liquid mixture; (2) spray drying the liquid mixture to form a first plurality of particles having a size in a range from about 0.5 to about 10 micrometres or in a range from about 0.5 to about 5 micrometres; and (3) milling the first plurality of particles to form a second plurality of particles. Preferably the milling unit operation is a fluid energy milling unit operation that reduces the size of the particles.

It has been found that preparing particles comprising nicotine by spray drying and then milling (especially fluid energy milling) could improve the inhalation experience or mitigate or reduce perceived harshness or a cough reflex associated with inhaling spray dried nicotine particles. The examples below illustrate that that the perceived feel during inhalation of the spray dried and further milled nicotine particles (with no cough suppressant such as menthol) compares favourably to spray dried and unmilled nicotine particles with 5% menthol cough suppressant.

The plurality of particles may be free of a cough suppressant material. The plurality of nicotine particles may comprises less than 5%, or less than 1%, or less than 0.1% by weight of cough suppressant (such as menthol), or be free of cough suppressant (such as menthol).

The liquid carrier may be water, for example. The liquid mixture is flowable. The liquid mixture is configured to flow through an atomization or atomizer nozzle to form a first plurality of particles. Then the first plurality of particles is fluid energy milled to form the precise size distribution of second plurality of particles, described herein.

The plurality of particles described herein may form a dry powder composition and be packaged for consumption. The particles described herein may form a dry powder composition and be packaged in an inhalation delivery consumable element or contained within an inhalation delivery consumable element. An inhalation delivery consumable element may be a capsule, for example. The capsule may be by disposed in an inhalation device, such as a dry powder inhaler. The inhalation device may pierce the capsule and the particles may be entrained in the inhalation air for delivery to the lungs of a consumer.

The plurality of particles or dry powder composition described herein and the inhalation delivery consumable element may be free of, or substantially free of carrier particles. The plurality of particles described herein and the inhalation delivery consumable element may be free of, or substantially free of particles that are greater than about 20 micrometres, or greater than about 50 micrometres, or greater than about 100 micrometres.

The plurality of particles described herein may be processed at a reduced (as compared to conventional nicotine particles) temperature that may result in reduced product loss. The spray drying inlet temperature and the outlet temperature may be reduced. The spray drying atomization pressure may be in a range from about 3 to about 7 bar, or 4 to about 6 bar, or about 5 bar.

The spray drying inlet temperature may be about 140 degrees Celsius or less, or about 135 degrees Celsius or less, or about 130 degrees Celsius or less, or in a range from about 100 to about 150 degrees Celsius, or in a range from about 110 to about 140 degrees Celsius, or in a range from about 125 to about 135 degrees Celsius. The spray drying outlet temperature may be about 100 degrees Celsius or less, or about 95 degrees Celsius or less, or about 90 degrees Celsius or less, about 85 degrees Celsius or less, or about 80 degrees Celsius or less, or in a range from about 30 to about 90 degrees Celsius, or in a range from about 40 to about 90 degrees Celsius, or in a range from about 50 to about 85 degrees Celsius.

The second plurality of particles may be formed by fluid energy milling the first plurality of particles formed by the spray drying unit operation. The first plurality of particles may be processed with a fluid energy mill by colliding the first plurality of particles with each other to form the second plurality of particles or particles.

The first plurality of particles (formed by the spray drying process) may be fluid energy milled at a temperature of about 50 degrees Celsius or less, or about 40 degrees Celsius or less, or about 30 degrees Celsius or less, about 20 degrees Celsius or less, or about 10 degrees Celsius or less, or in a range from about −20 to about 40 degrees Celsius, or in a range from about −10 to about 30 degrees Celsius, or in a range from about 0 to about 30 degrees Celsius.

The reduction in particle size by fluid energy milling may be increased by fluid energy milling at lower temperatures. The particles may tend to be more brittle at lower temperatures, and may therefore fracture more readily so that the milled particles tend to be smaller at lower temperatures. The first plurality of particles (formed by the spray drying process) may be fluid energy milled at a temperature below room temperature, preferably at a temperature below about 20 degrees Celsius, or below about 10 degrees Celsius, or below about 0 degrees Celsius.

Fluid energy milling may be carried out at milling or grinding pressures between about 0.1 and about 12 bar. Varying the pressure allows control over the amount of particle size reduction. The milling pressure may be in a range from about 1 to about 7 bar, or about 2 to about 6 bar, or about 3 to about 5 bar, or about 4 bar. Particle feed pressure may be greater than the milling pressure. Feed pressure may be in a range from about 5 to about 13 bar, or about 5 to about 10 bar, or about 6 to about 8 bar, or about 7 bar.

Fluid energy milling may be carried out in two or more stages, to combine the beneficial effects of the milling at different pressures. The use of multiple steps may allow one to tailor the properties of the fluid energy milled particles to suit a particular inhaler device or to target particular parts of the lung.

An additive material can be combined with the first plurality of particles and processed in the fluid energy mill. Combining an additive material with the first plurality of particles may be termed "co-jet or co-fluid energy" milling. The additive may coat the particles, depending on the milling pressure.

The fluid energy mill may be any useful type of fluid energy mill. Useful fluid energy mills include, for example, an Atritor M3 Spiral jet mill, a AS50 Spiral jet mill, a MC50 Hosakawa Microniser, other spiral jet mills, pancake jet mills or opposed fluid bed jet mills. The feed rate for the fluid energy mill will depend on the size of the mill. Small spiral jet mills may use a feed rate of, for example, about 1 to about 4 g per minute, whilst industrial scale mills will have a feed rate in the order of kilograms per hour. Examples below utilize the Atritor M3 Spiral jet mill. This fluid energy mill provided at greater than about 90% product yield or less than about a 10% product loss.

The properties of the fluid jet milled particles may, to an extent, be tailored or adjusted by making changes to the fluid jet milling unit operation. For example, the degree of particle size reduction may be adjusted by changing the number of jets which are used in the fluid jet mill, or by adjusting their orientation, that is, the angles at which they are positioned.

All scientific and technical terms used herein have meanings commonly used in the art unless otherwise specified. The definitions provided herein are to facilitate understanding of certain terms used frequently herein.

As used herein, the singular forms "a", "an", and "the" encompass embodiments having plural referents, unless the content clearly dictates otherwise.

As used herein, "or" is generally employed in its sense including "and/or" unless the content clearly dictates otherwise. The term "and/or" means one or all of the listed elements or a combination of any two or more of the listed elements.

As used herein, "have", "having", "include", "including", "comprise", "comprising" or the like are used in their open ended sense, and generally mean "including, but not limited to". It will be understood that "consisting essentially of", "consisting of", and the like are subsumed in "comprising," and the like.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the disclosure, including the claims.

FIG. 1 is a schematic flow diagram of an illustrative method 100 of forming the particles 135. The method 100 includes combining nicotine 102, a sugar 104, and an amino acid or peptide 106 in a liquid carrier to form a liquid mixture 115 at block 110. Then, at block 120, the liquid mixture 115 is spray dried to form a first plurality of particles 125. Then the first plurality of particles 125 is milled at block 130 (fluid energy milled, for example) to form a second plurality of particles 135.

EXAMPLES

All the examples (except Table 3 examples) are formulated by combining nicotine base and acid in water (at the specified ratio) to form a stable nicotine salt solution. Then the sugar and amino acid (leucine) is combined with the nicotine salt solution to form a liquid mixture. Then the liquid mixture is atomized and dried to form dry particles that are collected to from the dry powder composition.

The Table 3 examples are formulated by combining a nicotine free base with sugar and amino acid (leucine) to form a liquid mixture. Then the liquid mixture is atomized and dried to form dry particles that are collected to from the dry powder composition.

The spray dryer was a Buchi B-290 spray dryer (available from Buchi Corp., DE, USA). The liquid mixture was provided to the spray dryer at a flow rate of 2 ml/min at 5 bar atomization pressure. The outlet temperature was about 80 degrees Celsius for examples utilizing trehalose. Table 1 below describes lactic acid nicotine powder formulations. Table 2 below describes pyruvic acid nicotine powder formulations. Table 3 below describes no acid nicotine powder formulations. Table 4 reports the particle size distribution of various examples.

TABLE 1

Lactic Acid Nicotine Powder Formulations

| Example | Formulation | pH of powder solution | Comments |
|---|---|---|---|
| L1 | 10% Nicotine, Lactic acid (1:1), 85% Trehalose | 7.3 | Small amount of powder adhering to spray dryer surface |
| L2 | 15% Nicotine, Lactic acid (1:1), 77% Trehalose | 7.0 | Small amount of powder adhering to spray dryer surface |
| L3 | 10% Nicotine, Lactic acid (1:1), 80% Trehalose, 5% Leucine | 7.5 | Free flowing powder-no adherence |
| L4 | 15% Nicotine, Lactic acid (1:1), 72% Trehalose, 5% Leucine | 7.1 | Free flowing powder-no adherence |
| L5 | 20% Nicotine, Lactic acid (1:1), 64% Trehalose, 5% Leucine | | Free flowing powder-no adherence |

TABLE 2

Pyruvic Acid Nicotine Powder Formulations

| Example | Formulation | pH of powder solution | Comments |
|---|---|---|---|
| P1 | 10% Nicotine, Pyruvic acid (0.6:1), 87% Trehalose | 7.5 | Powder adhering to spray dryer surface, cohesive powder |
| P2 | 15% Nicotine, Pyruvic acid (0.6:1), 80% Trehalose | 7.8 | Cohesive powder, some static charge |
| P3 | 10% Nicotine, Pyruvic acid (0.6:1), 82% Trehalose, 5% Leucine | 7.7 | Free flowing powder-no adherence, some static charge |
| P4 | 15% Nicotine, Pyruvic acid (0.6:1), 75% Trehalose, 5% Leucine | 7.8 | Free flowing powder-no adherence |
| P5 | 20% Nicotine, Pyruvic acid (0.6:1), 68% Trehalose, 5% Leucine | 7.7 | Free flowing powder-no adherence |

TABLE 3

No Acid Nicotine Powder Formulations

| Example | Formulation | pH of powder solution | Comments |
|---|---|---|---|
| N1 | 10% Nicotine, 90% Trehalose | 9.3 | Some powder adhering to spray dryer surface |
| N2 | 15% Nicotine, 85% Trehalose | 9.5 | Some powder adhering to spray dryer surface |
| N3 | 10% Nicotine, 85% Trehalose, 5% Leucine | 8.6 | Free flowing powder-no adherence, some static charge |
| N4 | 15% Nicotine, 80% Trehalose, 5% Leucine | 8.7 | Free flowing powder-no adherence |
| N5 | 20% Nicotine, 75% Trehalose, 5% Leucine | 8.8 | Free flowing powder-no adherence |

TABLE 4

Particle Size Distribution-reported in micrometres

| Example | $X_{10}$ | $X_{50}$ | $X_{90}$ | VMD |
|---|---|---|---|---|
| L1 | 0.65 | 1.43 | 3.54 | 1.81 |
| L2 | 0.68 | 1.62 | 3.75 | 1.97 |
| L3 | 0.76 | 1.89 | 3.86 | 2.14 |
| L4 | 0.92 | 2.14 | 3.99 | 2.35 |
| L5 | 0.78 | 1.95 | 3.90 | 2.19 |
| P1 | 0.67 | 1.54 | 3.47 | 1.85 |
| P2 | 0.67 | 1.53 | 3.54 | 1.86 |
| P3 | 0.66 | 1.48 | 3.54 | 1.84 |
| P4 | 0.72 | 1.78 | 3.79 | 2.06 |
| P4 | 0.65 | 1.43 | 3.54 | 1.81 |
| N1 | 0.68 | 1.62 | 3.75 | 1.97 |
| N2 | 0.76 | 1.89 | 3.86 | 2.14 |
| N3 | 0.92 | 2.14 | 3.99 | 2.35 |
| N4 | 0.78 | 1.95 | 3.90 | 2.19 |
| N5 | 0.67 | 1.54 | 3.47 | 1.85 |

$X_{10}$ refers to size of particle where 10% of particles, by volume, are less than this size.

$X_{50}$ refers to size of particle where 50% of particles, by volume, are less than this size.

$X_{90}$ refers to size of particle where 90% of particles, by volume, are less than this size.

VMD refers to volume mean diameter.

Particle size distribution described herein was determined by Sympatec laser sizing, Andersen Cascade Impactation, and scanning electron microscopy.

TABLE 5

Further Formulations

| Example | Formulation | $X_{10}$ | $X_{50}$ | $X_{90}$ | VMD | MMAD |
|---|---|---|---|---|---|---|
| 1 | 10% Nicotine, Lactic Acid (1:1), 80% Trehalose, 5% Leucine | 0.92 | 2.17 | 4.15 | 2.4 | 3.8 |
| 2 | 10% Nicotine, Pyruvic Acid (1:0.6), 82% Trehalose, 5% Leucine | 1.04 | 2.56 | 5.08 | 2.9 | 4.0 |
| 3 | 10% Nicotine, Citric Acid (1:0.25), 82% Trehalose, 5% Leucine | 0.81 | 2.34 | 5.48 | 2.8 | 3.5 |
| 4 | 10% Nicotine, Aspartic Acid (1:0.6), 80% Trehalose, 5% Leucine | 0.82 | 2.24 | 4.96 | 2.6 | 4.2 |

Fluid Energy Milling Examples

The following examples are formulated as described above. Example 5 includes 5% wt menthol that is dissolved in ethanol and added to the liquid mixture. Example 6 is free of menthol.

The liquid mixture is atomized and dried with a spray dryer to form dry particles that are then fluid energy milled to from the dry powder composition.

The spray dryer was a Buchi B-290 spray dryer (available from Buchi Corp., DE, USA). The liquid mixture was provided to the spray dryer at a flow rate of 2 ml/min at 5 bar atomization pressure. The outlet temperature was about 80 degrees Celsius for examples utilizing trehalose.

The fluid energy mill was an Atritor M3 Fluid Energy Mill (available from Atritor Limited, England). The feed rate to the mill was about 3 grams per minute, using a compressed air driven venture feed at a pressure of about 7 bar and a milling pressure of about 4 bar, at room temperature. Example 5 was milled to create Example 5M and Example 6 was milled to create Example 6M.

TABLE 6

Nicotine Powder Formulations

| Example | Formulation | pH of powder solution |
|---|---|---|
| 5 | 5% Nicotine, Lactic Acid (1:1), 82% Trehalose, 5% Leucine, 5% Menthol | 7.3 |
| 6 | 5% Nicotine, Lactic Acid (1:1), 82% Trehalose, 5% Leucine | 7.2 |

Example 5 and Example 6 are then fluid energy milled as described above. Prior to fluid energy milling Example 6 had a respirable particle fraction of 52% (able to reach the lungs during inhalation). After fluid energy milling Example 6M had a respirable particle fraction of 70% (able to reach the lungs during inhalation).

TABLE 7

Particle Size Before and After Fluid Energy Milling

| Example | MMAD |
|---|---|
| 5 | 3.24 |
| 6 | 3.74 |
| 5M | 2.16 |
| 6M | 2.54 |

Table 8 reports particle size distribution immediately following (t=0) and 7 days (t=7) following spray drying and fluid energy milling. Storage conditions were 40 degrees Celsius and 75% relative humidity (RH) for seven days.

TABLE 8

| Example | X10 | X50 | X90 | VMD | Moisture Content |
|---|---|---|---|---|---|
| 5 t = 0 | 0.74 | 1.79 | 3.61 | 2.02 | 2.59 |
| 5 t = 7 | 0.74 | 1.80 | 3.66 | 2.05 | 2.32 |
| 5M t = 0 | 0.62 | 1.14 | 2.32 | 1.33 | 2.32 |
| 5M t = 7 | 0.62 | 1.19 | 2.50 | 1.14 | 2.98 |
| 6 t = 0 | 0.82 | 2.03 | 4.03 | 2.27 | 2.77 |
| 6 t = 7 | 0.80 | 2.03 | 4.05 | 2.27 | 3.02 |
| 6M t = 0 | 0.65 | 1.34 | 2.80 | 1.56 | 2.94 |
| 6M t = 7 | 0.64 | 1.32 | 2.80 | 1.56 | 2.99 |

Expert panel tests were conducted on Example 5 and Example 6 and Example 6M. Example 6M and Example 5 were deemed to be substantially equal in perceived inhalation feel as compared to Example 6.

The invention claimed is:

1. A dry powder composition, comprising:
    a plurality of particles formed of nicotine, a sugar, and an amino acid, wherein about 90% by volume of the particles have a particle size of less than about 2.8 micrometres, and about 50% by volume of the particles have a particle size of less than about 1.35 micrometres, and about 10% by volume of the particles have a particle size of less than about 0.65 micrometres.

2. The dry powder composition according to claim 1, wherein the nicotine comprises nicotine lactate, nicotine pyruvate, nicotine citrate, nicotine aspartate, nicotine bitartrate, nicotine salicylate, nicotine fumarate, nicotine monopyruvate, nicotine glutamate, nicotine hydrochloride, or a combination thereof.

3. The dry powder composition according to claim 1, comprising about 5 to about 15 wt % nicotine.

4. The dry powder composition of claim 1, comprising about 60 wt % to about 95 wt % sugar.

5. An inhalation delivery consumable element containing the dry powder composition of claim 1.

6. The dry powder composition of claim 1, comprising about 70 wt % to about 90 wt % sugar.

7. The dry powder composition of claim 1, comprising about 1 wt % to about 10 wt % nicotine.

8. The dry powder composition of claim 1, comprising about 70 wt % to about 90 wt % sugar, about 1 wt % to about 10 wt % leucine, and about 1 wt % to about 10 wt % nicotine.

9. The dry powder composition of claim 8, further comprising menthol.

10. The dry powder composition of claim 1, wherein the sugar comprises lactose, sucrose, raffinose, trehalose, fructose, dextrose, glucose, maltose, mannitol, or a combination thereof.

11. The dry powder composition of claim 1, wherein the sugar comprises mannitol.

12. The dry powder composition of claim 1, wherein the sugar comprises trehalose.

13. The dry powder composition of claim 1, wherein the amino acid comprises leucine.

14. The dry powder composition of claim 1, wherein the plurality of particles consist of nicotine salt, sugar, amino acid, and optionally menthol.

15. The dry powder composition of claim 14, wherein the plurality of particles contain about 70 wt % to about 90 wt % sugar and about 1 wt % to about 10 wt % nicotine.

16. The dry powder composition of claim 1, wherein the plurality of particles is prepared by spray drying from a liquid mixture comprising the nicotine, the sugar, and the amino acid, and a liquid carrier.

17. The dry powder composition of claim 16, wherein the nicotine, the sugar, and the amino acid are dissolved in the liquid carrier prior to spray drying.

18. The dry powder composition of claim 17, wherein the spray drying is performed using an inlet temperature of 140 degrees Celsius or less and an outlet temperature of 100 degrees Celsius or less.

19. The dry powder composition of claim 18, wherein the outlet temperature is 80 degrees Celsius or less.

20. The dry powder composition of claim 16, wherein the plurality of particles is prepared by fluid energy milling after spray drying.

\* \* \* \* \*